US010515060B2

(12) United States Patent
de Vries et al.

(10) Patent No.: US 10,515,060 B2
(45) Date of Patent: Dec. 24, 2019

(54) METHOD AND SYSTEM FOR GENERATING A MASTER CLINICAL DATABASE AND USES THEREOF

(71) Applicant: Medidata Solutions, Inc., New York, NY (US)

(72) Inventors: Glen de Vries, New York, NY (US); Michelle Marlborough, Brooklyn, NY (US); Christopher Bound, Doylestown, PA (US); Joshua Hartman, Conshohocken, PA (US); Jeevan Pendli, Richmond, VA (US)

(73) Assignee: Medidata Solutions, Inc., New York, NY (US)

( * ) Notice: Subject to any disclaimer, the term of this patent is extended or adjusted under 35 U.S.C. 154(b) by 546 days.

(21) Appl. No.: 14/066,421

(22) Filed: Oct. 29, 2013

(65) Prior Publication Data

US 2015/0120725 A1 Apr. 30, 2015

(51) Int. Cl.
*G06F 16/22* (2019.01)
*G06Q 50/24* (2012.01)
*G06Q 10/10* (2012.01)
*G06Q 50/22* (2018.01)
*G16H 10/20* (2018.01)
(Continued)

(52) U.S. Cl.
CPC .............. *G06F 16/22* (2019.01); *G06F 16/28* (2019.01); *G06F 19/00* (2013.01); *G06Q 10/10* (2013.01); *G06Q 50/22* (2013.01); *G06Q 50/24* (2013.01); *G16H 10/20* (2018.01)

(58) Field of Classification Search
CPC .... G06F 17/30312; G06F 16/22; G06F 16/28; G06F 19/00; G16H 10/20; G06Q 10/10; G06Q 50/22; G06Q 50/24
See application file for complete search history.

(56) References Cited

U.S. PATENT DOCUMENTS 7,752,060 B2 7/2010 Hicks et al.
8,515,987 B1 8/2013 Jain et al.
(Continued)

FOREIGN PATENT DOCUMENTS

KR 101226056 B1 1/2013
WO 2003/021485 A2 3/2003

OTHER PUBLICATIONS

Melton et al. Jun. 2010, http://www.ncbi.nlm.nih.gov/pmc/articles/PMC2995709/pdf/amiajnl2238.pdf, p. 1.*
(Continued)

*Primary Examiner* — Matthew J Ellis
(74) *Attorney, Agent, or Firm* — Steptoe & Johnson LLP; Robert Greenfeld

(57) ABSTRACT

A method and system for generating a master clinical database from disparate sources, including public databases, private databases, and data from users, correlating the received data, determining a degree of confidence in and requesting and seeking confirmation of any data matched from the correlated data. The invention may identify key time points and users from whom to seek and receive confirmation of correlated data. The invention may be utilized to create a cross-trial, cross-sponsor, clinical master database that maintains appropriate user, subject and data confidentiality and privacy and which may be utilized to facilitate study design collaboration.

17 Claims, 5 Drawing Sheets

(51) Int. Cl.
*G06F 16/28* (2019.01)
*G06F 19/00* (2018.01)

(56) References Cited

U.S. PATENT DOCUMENTS

| | | | |
|---|---|---|---|
| 8,751,252 B2* | 6/2014 | Chamberlain | G06F 19/321 |
| | | | 705/2 |
| 2002/0010715 A1* | 1/2002 | Chinn et al. | 707/514 |
| 2003/0126156 A1 | 7/2003 | Stoltenberg et al. | |
| 2004/0078216 A1* | 4/2004 | Toto | 705/2 |
| 2004/0093240 A1 | 5/2004 | Shah | |
| 2004/0158562 A1* | 8/2004 | Caulfield | G06F 17/30303 |
| 2005/0165734 A1* | 7/2005 | Vicars et al. | 707/2 |
| 2006/0149593 A1 | 7/2006 | Wager | |
| 2009/0198686 A1* | 8/2009 | Cushman et al. | 707/5 |
| 2011/0099193 A1* | 4/2011 | Jensen | 707/769 |
| 2012/0072464 A1 | 3/2012 | Cohen | |
| 2013/0151280 A1 | 6/2013 | Thiers et al. | |

OTHER PUBLICATIONS

The International Search Report and Written Opinion of the International Searching Authority, PCT/US2014/062719, dated Jan. 26, 2015.
EPO Supplementary Search Report and Office Action, App. No. 14857773.7, dated Jun. 14, 2017.
EPO Office Action, App. No. 14857773.7, dated Jul. 27, 2018.

* cited by examiner

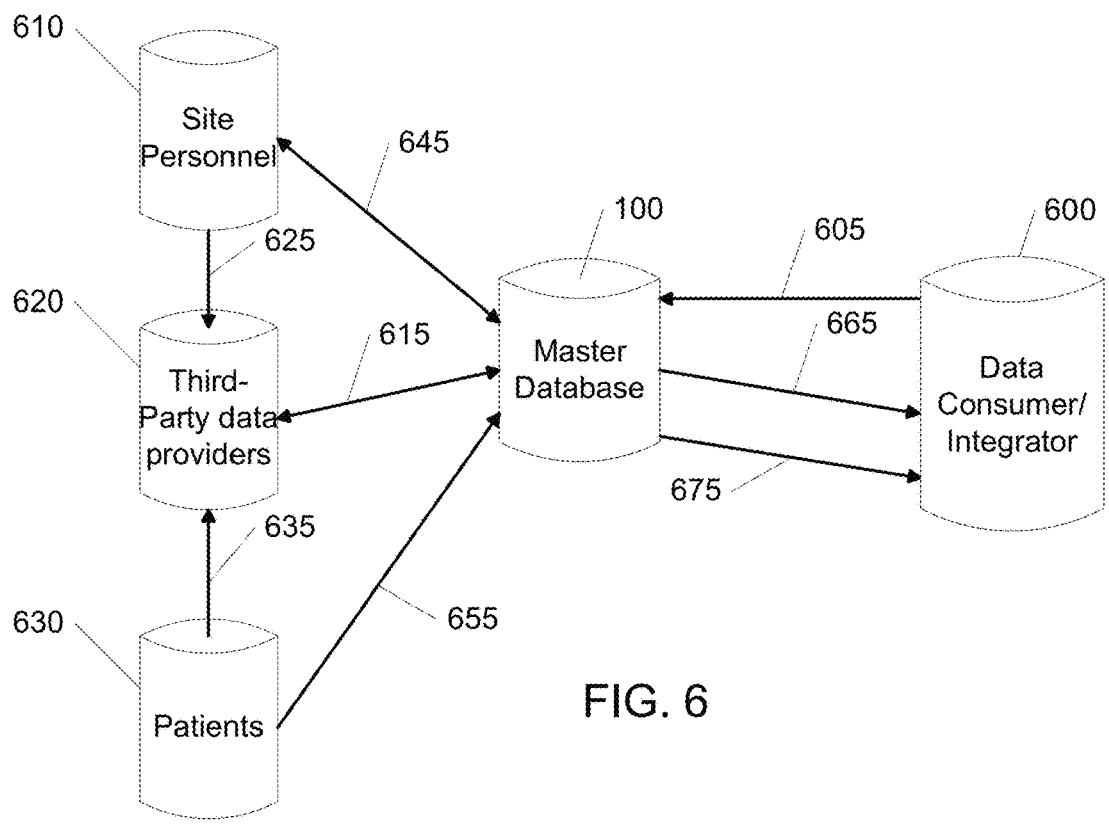

METHOD AND SYSTEM FOR GENERATING A MASTER CLINICAL DATABASE AND USES THEREOF

BACKGROUND

Clinical trials typically involve numerous subjects, many test sites, extensive planning and coordination, and are very expensive to run. Pharmaceutical development continues to be under pressure to reduce operational costs while maintaining or increasing scientific values. In recent years, one approach to reducing costs of clinical trials is using electronic data capture (EDC) rather than recording all trial data on paper. Another approach is to remotely monitor some sites, rather than sending site monitors to physically visit all sites to confirm adherence to the design of the trial and/or good clinical practice.

One area of clinical development that has not been adequately addressed is the coordination of various sources of data from across different clinical trials and even different sponsors in order to facilitate future trials. For example, starting up a trial, which involves selecting appropriate sites, investigators and subjects, remains a laborious and oftentimes repetitive task for trial sponsors (pharmaceutical companies), or their contract research organizations (CROs). Similarly, with appropriate data coordination, site and investigator collaboration may be enabled, and through feedback from other PIs or site personnel, improved protocol design collaboration may be facilitated.

BRIEF DESCRIPTION OF THE DRAWINGS

FIG. 6 is a block diagram illustrating a way in which a master database may be used, according to an embodiment of the present invention;

FIG. 7 is chart illustrating key time points at which users may have or may be provided with incentives to provide, update or confirm information, according to an embodiment of the present invention;

Figure 1:
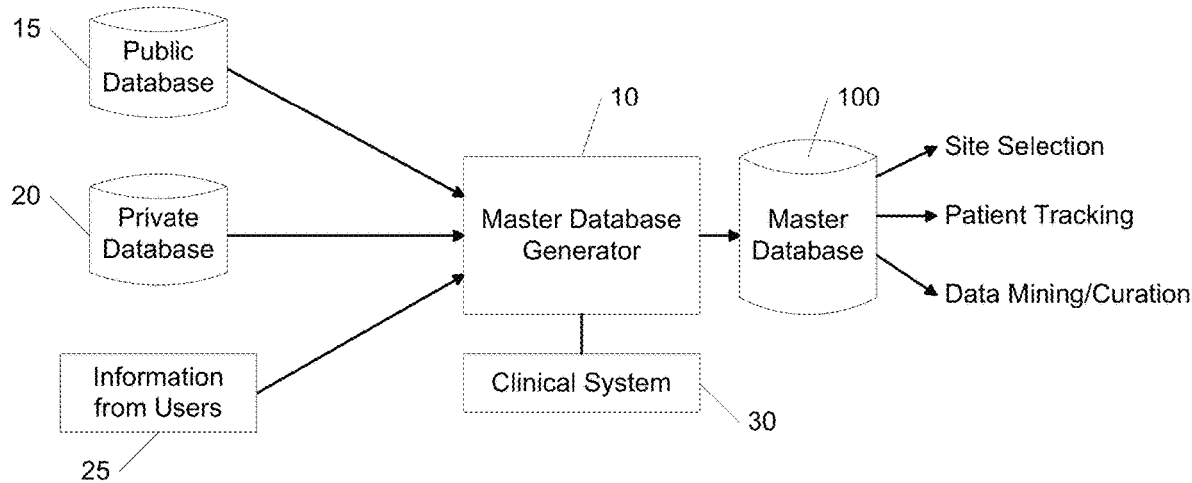
FIG. 1 is a block diagram of a master database generator according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Embodiments of the present invention may be used with respect to clinical trials, but the invention is not to be limited to such embodiments. Currently the typical process by which a pharmaceutical company or a contract research organization (a CRO) selects a site and/or a principal investigator (PI) for participation in a clinical trial includes finding data about the site or PI from existing spreadsheets, contacting key opinion leaders to determine which PIs provide appropriate sites, confirming PIs who are interested, qualified and available, having sites and PIs upload documents such as curricula vitae (CVs), confidential disclosure agreements (CDAs), clinical trial agreements (CTAs), and/or performing qualification feasibility, e.g., a questionnaire sent by sponsors to confirm sites are adequately equipped to conduct a trial. For a medium-sized pharmaceutical company that may perform on the order of 20 clinical trials in a year (in all phases) and spend $1 billion to $2 billion, a decrease of even 10 days in study startup time could save $20 million to $40 million per year. The present invention may be used to reduce clinical study start-up costs by generating and maintaining a cross-sourced database of sites, site personnel, subjects, and site histories and performance. Systems utilizing such a database could engage physicians (e.g., PIs) and sponsors in a collaboration prior to, during, or after the conduct of a clinical trial, including the review of study protocols to avoid unnecessary, expensive amendments mid-study and other uses described herein. Such collaboration has other benefits, because the participation of better performing sites and investigators (e.g., those having histories of performing well in previous studies) is likely to lead to better data and a more efficiently and economically conducted trial. In an industry in which a significant fraction of sites could be considered "underperforming," reducing this fraction will result in significant savings for a given clinical trial.

Reference is now made to FIG. 1, which is a block diagram of a master database generator according to an embodiment of the present invention. In FIG. 1, master database generator 10 may take as inputs data from disparate sources, e.g., data from public databases 15, data from private databases 20, and data from users 25. Such data may differ in data type, data structure, as well as native naming conventions and accessibility. Public databases 15 supplying information may include PubMed, which includes scholarly articles, social media sites such as LinkedIn® and Facebook®, professional or trade association databases, such as maintained by the American Medical Association (AMA), and governmental databases such as the National Provider Identifier (NPI) and Drug Enforcement Agency (DEA) databases. Private database information may include information kept by a master database operator, such as a supplier of software for managing clinical trials, a sponsor or a CRO, which is not publicly accessible and which may include information about previous clinical trial studies and sites, site personnel such as doctors, nurses, principal investigators (PIs), and patients or subjects. Information from users of the present invention, such as site personnel, CRAs and monitors, is generally received in the form of answers to questions posed at key time points of user interaction with the present system. Key time points may be prior to or during a clinical trial, e.g., study design, site selection, subject enrollment, study execution, and site payment, and may correspond with incentives users may have to provide, update or confirm information.

Master database generator 10 may generate a master database such as database 100. Database 100 may have a number of uses including clinical site selection, patient tracking, and data mining, all of which may reduce costs for clinical trials. Master database generator 10 may also function in connection with a clinical system 30, which system may contain or provide workflow instructions, users, user roles, and any key time points related to the workflow of one or more clinical applications. (As used herein, a workflow includes instructions for users to complete tasks using one or more software applications at various points in time or sequences.) Such data provided by clinical system 30 may facilitate the correlation or confirmation of received data 15, 20 or 25, as described further with reference to FIGS. 2 and 3.

Figure 2:
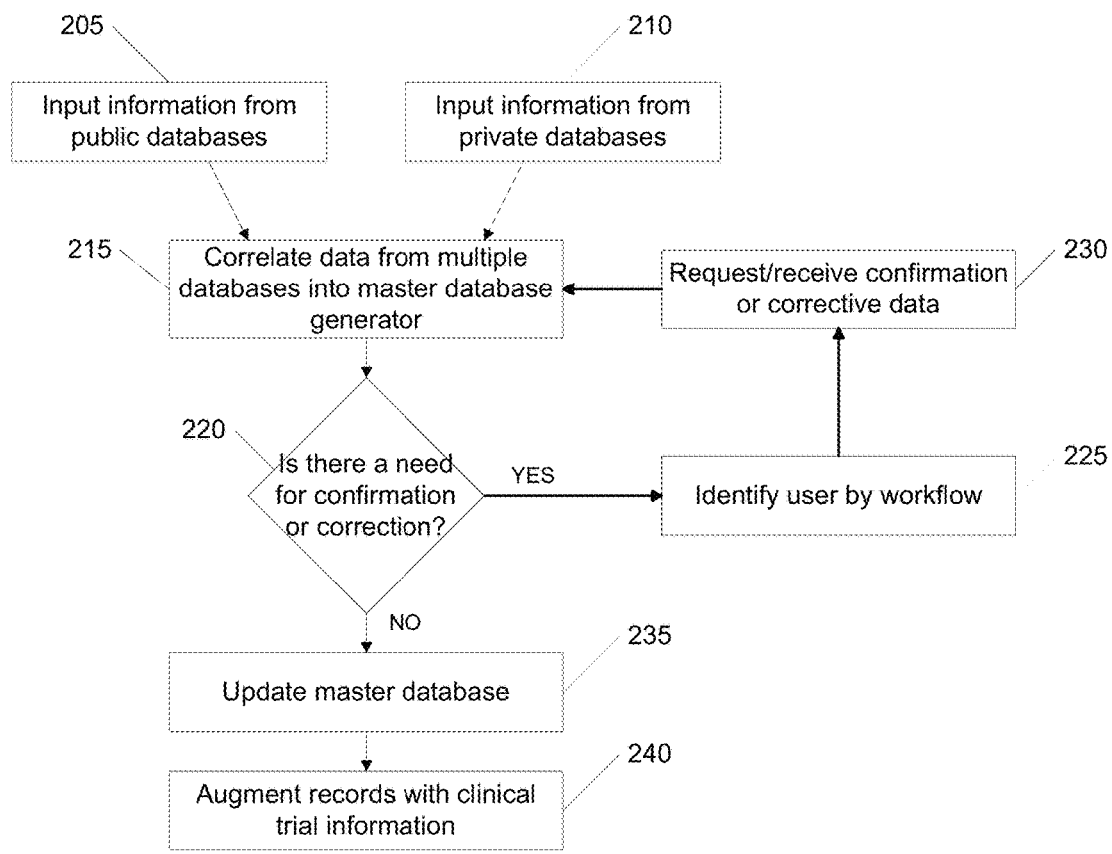
FIGS. 2 and 3 are flowcharts illustrating how a master database may be generated according to embodiments of the present invention.

FIG. 2 is a flowchart illustrating how a master database may be generated according to an embodiment of the present invention. In operations 205 and 210, information from public or private databases, respectively, may be received by the master database generator 10 via, inter alia, application programming interface (API) calls. It should be noted that information in private or internal databases 20 may be subject to confidentiality laws and/or practices, and having such information correlated or maintained in a master database 100 by an accredited or certified database operator may be more beneficial than if such information were available in multiple databases operated or maintained by less trustworthy entities.

After the information for the master database has been collected from public and private databases and input into the master database generator, the records in the database may begin to be correlated or associated in operation 215. This process may include matching up names, addresses, credentials, and other identifying information (such as NPI numbers or social security numbers) of people and entities, or matching clinical or operational data related to studies or their management.

Figure 3:
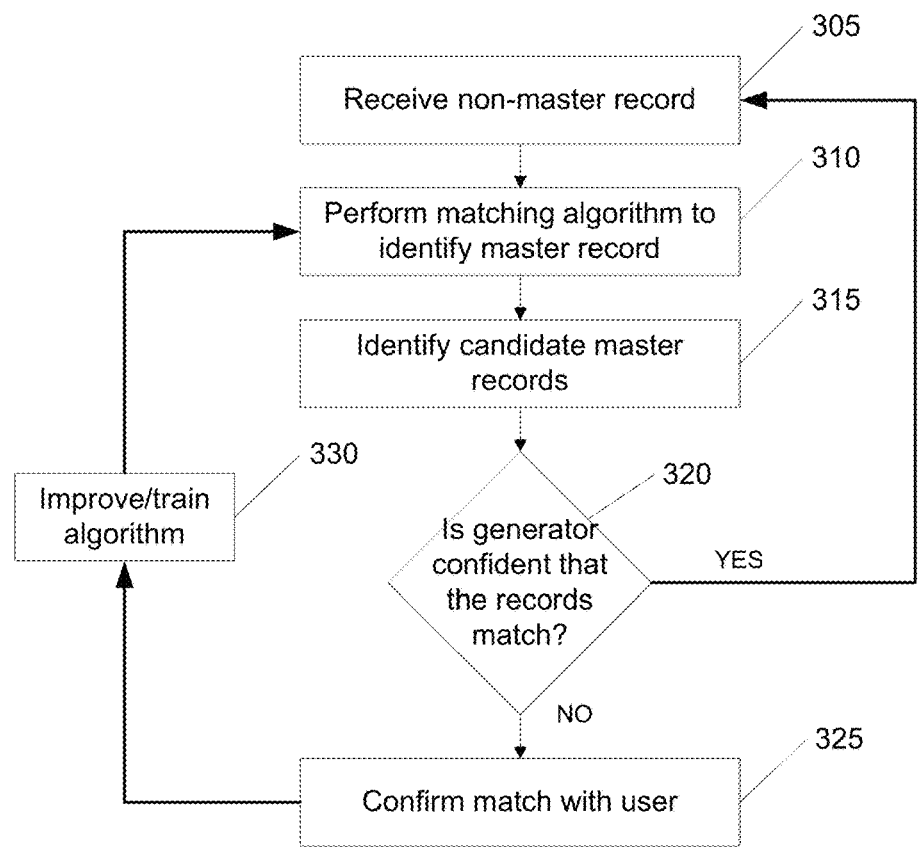

One way of performing such correlation is shown in the flowchart in FIG. 3. In that process, in operation 305, the database generator 10 receives a non-master record. A non-master record is generally any data which is not yet designated as confirmed, trustworthy or "master" by the present invention as so identified by the Master Database Generator 10. In operation 310, the database generator may execute a matching algorithm to identify corresponding records in master database 100, and in operation 315 may identify such corresponding, or candidate master, records. Such algorithms may be available commercially, such as from a software vendor like SAS, R language or natural language processing (NLP) tools such as GATE, NLTK or Stanford Named Entity Recognizer (NER), custom-developed software such as TrialX.com, or may be developed by a database operator. In operation 320, the database generator system may perform calculations to determine a degree of confidence in the matching or correlation between non-master and candidate master records. If the confidence is high, for example above a specific (optionally user adjustable) threshold confidence level, then the system may loop back to operation 305 to receive the next non-master record. If the confidence is low, the system may then prompt the database generator of the need to receive confirmation of the match, or corrective data, from a user in operation 325. Such confirmation may occur in relation to the later steps in the flowchart in FIG. 2, as discussed below, or may be performed by a master database operator through a curation user interface to master database 100 (not shown in figures). In either case, confirmation by or corrective data from a user may allow the matching algorithm to improve or be trained in operation 330. This "supervised" machine learning technique will allow for the algorithm to generalize from the curated data to unseen situations in a reasonable way. Using Empirical Risk Minimization (or some other minimization technique), the supervised learning algorithm seeks a function that uses a set of training examples, i.e. the curated data, and minimizes the risk of this function as defined by the loss of predicting the correct output.

Figure 9:
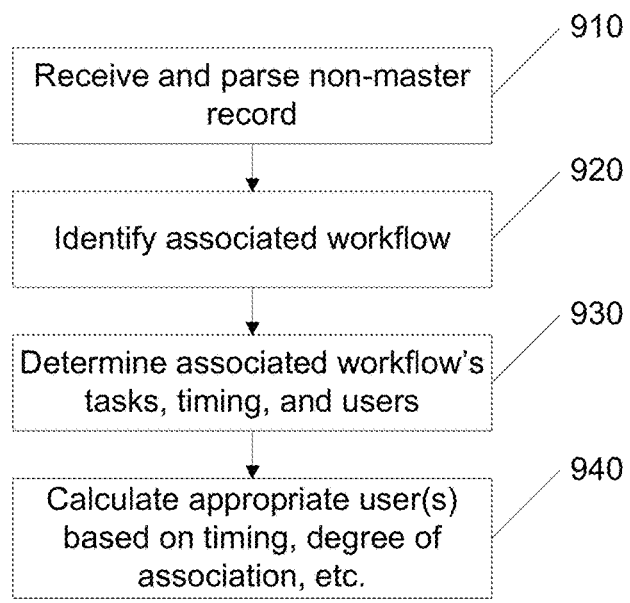
FIG. 9 is a flowchart illustrating identification of appropriate users, according to an embodiment of the present invention.

As part of the correlation or matching of data from multiple, disparately-sourced (e.g., public and/or private) databases to generate a master database 100, the master database generator 10 in operation 220 (in FIG. 2) may be used to identify a need to receive confirmation of a match or to receive records. A need to receive confirmation may be determined on the basis of the degree of confidence in the matching operation; where data matches, it may not require further confirmation. However, for some types of data, depending on their source, confirmation may be required even where a match to existing data exists. In operation 225, the master database generator may then be used to identify those appropriate users most likely to be able to provide confirmation or corrective data. Identification of appropriate users may be accomplished by determining a workflow received from clinical system 30, which will utilize the non-master record, and calculating on the basis of that workflow (and/or master records contained in master database 100) users who are in a position to provide informative, correlatable data. In more detail, as shown in FIG. 9, master database generator 10 may receive (and if necessary to determine its data type) parse in operation 910 the non-master record, which non-master record may then be used to identify an associated workflow 920. In operation 930, master database generator 10 may then use (or decompose) the workflow associated with the non-master record to determine associated tasks, timing and users that, as part of the workflow, may be used in operation 940, to calculate appropriate user(s) based on those tasks and timing. For example, if the non-master record requiring confirmation concerns a clinical site (such as its address, its principal investigator, etc.), an associated workflow directed to setting up or investigating potential clinical sites for a clinical study may be identified and selected, and in operation 225, that workflow may be used as the basis to identify specific users who are personnel related to the site being investigated ("site personnel"). In operation 230, the appropriate users—the site personnel—may then be queried at a key time point (discussed further with respect to FIG. 7) to receive confirmation, or corrective data, regarding themselves, other personnel at the site, or about the site itself. Using responses to these questions, the database generator may correlate information with the master database in operation 215 and may then again in operation 220 identify whether a need exists to receive further confirmation of a match or to receive records. Where no such need exists, the master database may be updated in operation 235, e.g., with a confirmation that a record is a master record and/or with the received corrective data.

Besides the operations shown in FIGS. 2 and 3, other operations or series of operations are contemplated to generate a master database. Although directed to asking questions of site personnel, FIGS. 2 and 3 could also be used to correlate information from patients interested in being subjects in a clinical study, or to correlate data from data consumers or data integrators 600 (discussed further herein). Moreover, the actual order of the operations in the flowcharts is not intended to be limiting, and the operations may be performed in any practical order. For example, operations 205, 210 and 215 may not need to occur in that order or at the beginning of the process. Private information may be gathered first, or both public and private information may be collected in an interleaved format, both before and after master database is identifying a need for data to be confirmed or supplemented as part of operation 220. Also, the correlations occurring in operations 225 and 215 may involve the same or similar processes or steps, such as those shown in FIG. 3. The goal of the operations in FIGS. 2 and 3 is to show that a master database may be generated by inputting information from disparate sources, performing matching algorithms and/or other correlations on the records to ensure that the master database records are accurate, and to confirm such information periodically with site personnel who are determined to be in an advantageous position to ascertain or provide further confirmation of non-master records.

An example of the process occurring in operations 215, 220, 225, and 230 is that the system is trying to identify and correlate information for a "Dr. Robert Smith," who is a principal investigator. There may be a number of people named Dr. Robert Smith, so the system identifies the records associated with all those named Dr. Robert Smith and attempts to match records based on work and home address information, email addresses, middle name or initials, and background information (such as education or place of medical residency). If the confidence is not high regarding some information or if there are conflicts in the data, the system may ask site personnel questions designed to resolve the conflicts and confirm the identity of the correct Dr. Robert Smith. Other information investigated and questions asked may include credential and training information related to clinical studies (such as training in good clinical practice (GCP)) and identities of personnel working with Dr. Robert Smith. Once all these questions have been asked and confirmed, in operation 235, the master database is updated (e.g., a record may be updated indicating that a record is now confirmed as a master record, and/or with the current degree of confidence), and the master database operator has a high degree of confidence that the information in the database is correct and useful.

Once a master database with quality, confirmed data is set up, it may be augmented in operation 240 with information curated by the database operator. Curation may involve performing complex transactions with data, such as data mining. As contemplated herein, curation may involve associating a protocol or its required procedures with performance at various sites, i.e., surfacing a more contextual relationship that a mere performance metric, which relationship gives more utility or meaning to the data in the master database. In the clinical trial context, useful information may include the performance of the site relative to other sites in past studies, the performance of the site on various metrics that are monitored during a clinical trial, such as deviations from protocol, severe adverse events (SAEs), subject enrollment, dropouts, etc. Such curated data may also include patient feedback about the doctors/investigators, which may permit a later sponsor to select quality investigators. As another example, master database 100 may keep track of the kinds of patients that a certain site sees. In this example, a cancer hospital may see patients with different types of cancer, e.g., breast, bone, liver, and pancreatic cancer. The site may see many patients with breast, bone, and liver cancer, and the results for those patients are good, but it sees only a few patients with pancreatic cancer, and the results for those patients are mixed. Master database 100 would thus be able to better inform to a sponsor looking for a site to test a cancer drug.

Figure 4:
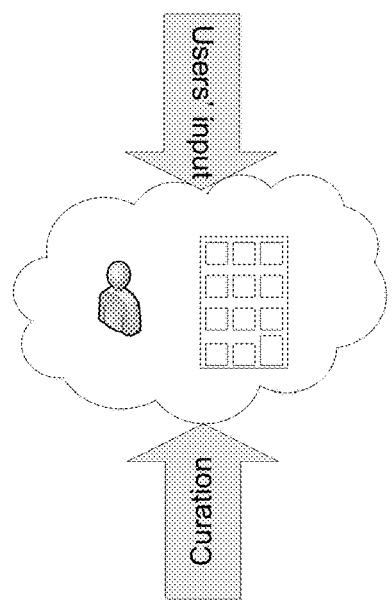
FIG. 4 is a schematic diagram illustrating the combination of curation and user input according to an embodiment of the present invention.

FIG. 4 is a schematic diagram illustrating the combination of curation and user input according to an embodiment of the present invention. After master database generator 10 receives data from private databases 20 and public databases 15, it can use information from users ("users' input" in FIG. 4) to help curate the data. Such data may include their users' certification status, training background, history as contributors to the design of or conduct of clinical trials, publications or other research, management of prior clinical trials, responsiveness to sponsor requests, feedback from other participants, etc. Then, when sites and/or patients are being selected for future trials, sponsors and the database operator may access the master database to reliably retrieve information concerning subjects and sites that may be good candidates for participation based on the data within the participants' and sites' records. Similarly, as described further herein, the use of curated data may facilitate site and PI collaboration for purposes such as improving protocol design. As part of embodiments of the invention and as further described herein with reference to the key time points shown in FIG. 7, the present invention may also take advantage of incentives that the users, including PIs, nurses, administrators, patients, site monitors, etc., may have to keep their data up to date.

Figure 5A:
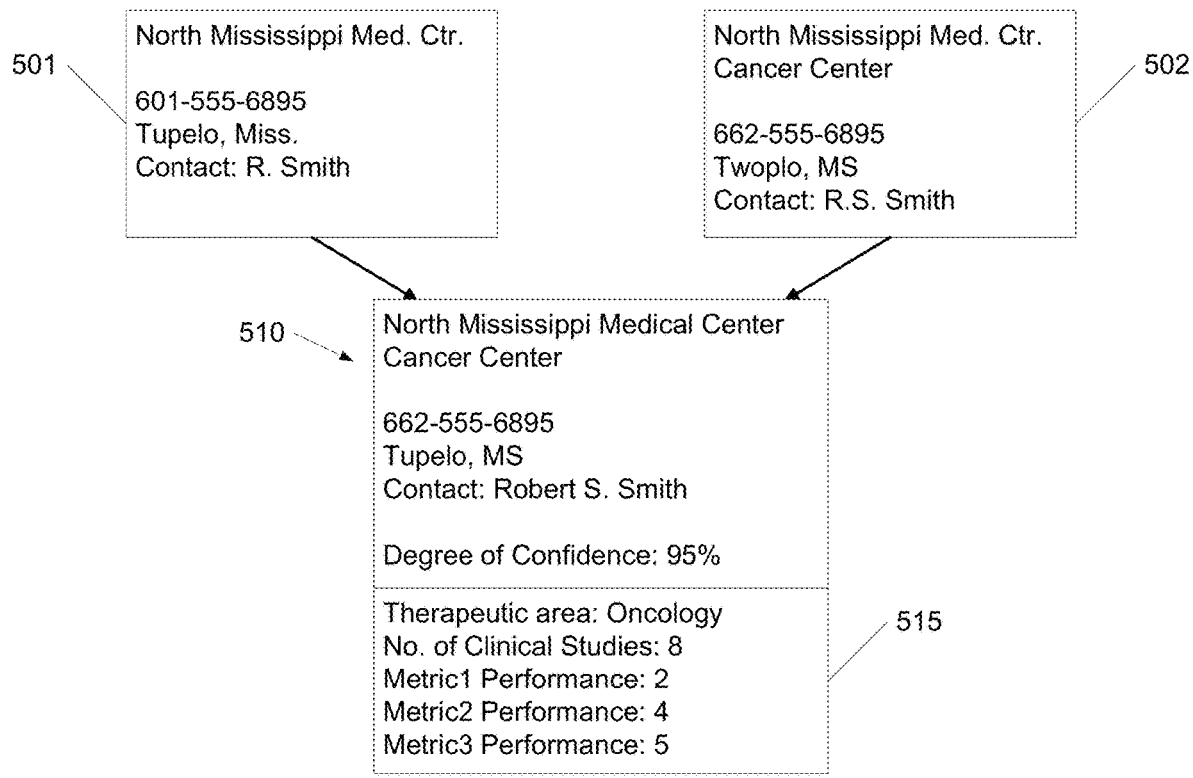
FIGS. 5A and 5B are diagrams of master records according to embodiments of the present invention.
Figure 5B:
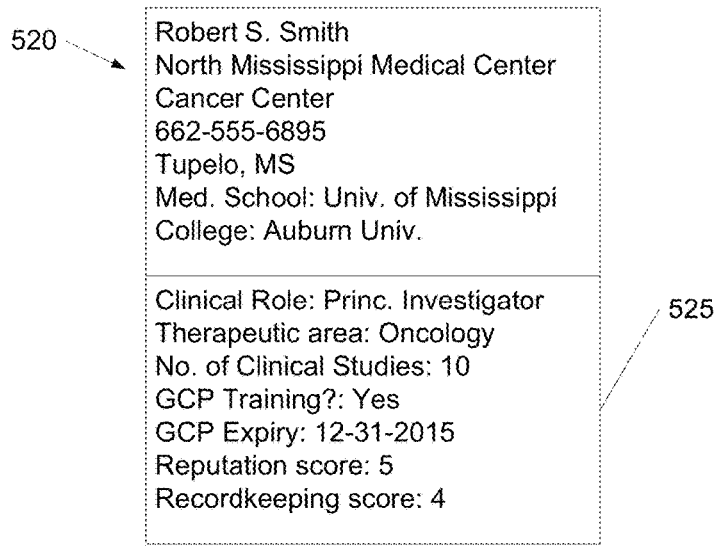

Further details of the operations performed in the flowcharts of FIGS. 2 and 3 and the curation of FIG. 4 are shown in FIGS. 5A and 5B. FIG. 5A shows how two records 501, 502 may be correlated to generate master site record 510. Records 501, 502 are site records, and may include the name of the test facility, phone number, address, and principal investigator. One or both of records 501, 502 may have come from different clinical studies or one or both may have come from a public or private database.

In FIG. 5A, all four pieces of information in records 501, 502 differ, but the matching algorithm may be able to determine that the facility name, phone number, and address refer to the same site. Master site record 510 reflects the correct nomenclature for these three items, namely, that the facility is the North Mississippi Medical Center Cancer Center, not just the "North Mississippi Med. Ctr." or "North Mississippi Medical Center"; the phone number is currently 662-555-6895, even if in the past the area code had been 601, because the current area code for Tupelo, Miss. is 662; and the correct names of the city and state are "Tupelo, Miss.," using the US Post Office's designation for Mississippi. As for the name of the PI, master database generator 10 may recognize that R. Smith and R. S. Smith may be the same person (at least within a confidence range), and/or it may ask the PI questions to confirm that, but may also ask for a complete first name so as to make the master record more accurate for the future, which is why master site record 510 includes the name "Robert S. Smith."

After generating master site record 510 with site information, additional information regarding clinical trials may be included in the record in area 515. In FIG. 5A, the therapeutic area is correlated (more than one therapeutic area could be listed) and a therapeutic sub-area, such as bone cancer, liver cancer, etc., could be correlated. A number of clinical trials conducted may also be included and would be incremented each time new information is input to master database generator 10. In addition, information regarding performance metrics may be included in master site record 510; in this case, the "score" is normalized from 0 through 5, but any suitable scale could be used. Metric1 could be severe adverse events (SAEs); Metric2 could be dropouts, and Metric3 could be deviations from protocol. Other information regarding the site may also be included, such as average enrollment, auto query rate, screen failure rate, etc.

There may be multiple types of master records in master database 100. FIG. 5A included an example of a master site record, but there could also be master records for personnel and organizations involved in the clinical trials, e.g., PIs, nurses, administrators, CRAs, CROs, laboratories and other third party vendors, and patients. FIG. 5B shows master PI record 520 for the PI associated with the site in master site record 510, namely Robert S. Smith. The record may include a facility where Dr. Smith performs his work, which may also be the site in master site record 510, but does not need to be. Master PI record 520 may include more than one facility, however. Master PI record 520 may also include the PI's educational background, medical training, and publications (not shown). For each type of data in master database 100, the key is that the data is either confirmed or is associated with a degree of confidence.

In addition, master PI record 520 may include clinical trial information 525, such as historical and/or performance data. This may include whether the PI took a training class (e.g., Good Clinical Practice (GCP)), how long the certification would last, what the PI's reputation was regarding operation of clinical trials, and how good a record keeper the PI was, etc.

After the master database is generated and augmented with additional information, it can be utilized by sponsors, CROs, and others who desire to use such information for, among other things, performing clinical trials. FIG. 6 is a block diagram illustrating a way in which such a master database may be used, according to an embodiment of the present invention. FIG. 6 shows master database 100 (possibly operated by the database operator) with some of its disparate sources of information as well as its uses. On the left side of FIG. 6 are site personnel 610, including doctors, e.g., principal investigators, nurses, an administrator, and other clinical trial personnel, third-party data providers 620, and patients 630. For example, data regarding site personnel 610 may include address and contact details, qualification information and performance data or metrics. Data regarding third-party data providers 620 may include black list information (such as data from the FDA's Clinical Investigator—Disqualification Proceedings database, listing clinical investigators subject to a disqualification action, including related regulatory documents such as NOOHs (notice of opportunity for hearing), NIDPOEs (notice of initiation of disqualification proceedings and opportunity to explain), etc.), FDA warning letters (correspondence that notifies regulated industry about violations that FDA has documented during its inspections or investigations), and FDA 1572 data (Statement of Investigator Form, whereby an investigator provides assurances of compliance with FDA regulations regarding a clinical trial), as well as data from sources such as clinilabs.com and tlo.com, etc. Data regarding patients 630 may include contact information, patient identifiers, including de-identified identifiers such as automatically generated identifiers, and demographic or clinical information. On the right side of FIG. 6 is data consumer/integrator 600, such as a sponsor, or a CRO, or other life sciences company. In some cases, master database 100 may act as an intermediary between data consumer/integrator 600 and site personnel 610, third-party data providers 620, and patients 630. As used herein, a data consumer/integrator 600 is not a master database operator.

The arrows in FIG. 6 represent information exchanges. Arrow 605 may represent information provided by data consumer/integrator 600 to master database 100 about sites and site personnel from previous studies. This information may comprise some of the private database information shown in FIG. 1, described with respect to operation 210 or operation 325.

Arrow 615 may represent information from third-party data providers 620 to master database 100. This information may comprise data from both public database 15 and private database 20 shown in FIG. 1 and described with respect to operations 205 and 210. For example, third-party public data providers may include PubMed, LinkedIn®, Facebook®, the AMA, NPI, and DEA. Third-party private data providers may include clinical data, safety-related data, clinical trial/operational data, electronic health records (EHR) data, and/or electronic medical records (EMR) data, which may not be made available to data consumer/integrator 600, but which may be made available to master database 100, because, e.g., the database operator may be able to provide assurances of confidentiality and anonymity regarding the records or the clinical data may be unblinded or aggregated.

Arrow 625 may represent information that site personnel 610 provide to third-party data providers 620, such as information found in PubMed, LinkedIn®, Facebook®, the AMA, NPI, and DEA, as well as information that site personnel 610 provide regarding training or other credentials but which may not be in a public database. Similarly, arrow 635 may represent information that patients 630 provide to third-party data providers 620, such as information found in LinkedIn®, Facebook®, as well as EHR and EMR data as described above which may not be in a public database.

Arrow 645 may represent information that master database 100 lacks, and the system or method of the present invention may request from site personnel 610 and information that site personnel 610 may provide to master database 100, such as informed consent documents (ICDs), which are typically stored at sites. Site personnel 610 may enter and/or update their information in master database 100, as was described generally in relation to the flowcharts in FIGS. 2 and 3. Similarly, arrow 655 may represent information that master database 100 seeks from patients 630 and information patients 630 may provide to master database 100, such as being available as trial subjects for other clinical trials. Information about patients 630 may be provided to master database 100 either by site personnel 610 via arrow 645 or by patients 630 via arrow 655.

Once information is in master database 100, subsets of such information may be made available by the master database operator to data consumer/integrator 600 via arrows 665 and 675. Arrow 665 may represent information that may comprise trial-specific data, such as contained in an EDC database, related only to a specific clinical study currently being conducted. Arrow 675 may represent information that may comprise a company-specific database, such as a CTMS database, related only to data consumer/integrator 600. Arrow 665 and 675 information may be maintained for data consumer/integrator 600 using master record indicators through either subscribing to master database 100 (using, for example, a "publish-subscribe" or "pub-sub" scheme) or using an API (application programming interface) call to master database 100.

The parts and blocks shown in FIGS. 1 and 6 are examples of parts that may comprise systems that generate master databases, and do not limit the parts or modules that may be included in or connected to or associated with the systems. For example, private and public databases may be accessed from the same location and master database 100 may be distributively stored. Shown in FIG. 1 is clinical system 30, but the invention may be used with data systems other than clinical systems. In FIG. 6, entities are not limited to the three sources shown on the left side. Moreover, although the above description says that data consumer/integrator 600 is not a master database operator, that may not always be the case.

As mentioned above, because of the confidentiality of various data in the life sciences and clinical trial area and the need to keep some information anonymous (including to retain blinding of clinical data), users may be limited in viewing information about others. For example, doctors may be able to see all or most information about the sites and the patients (such as clinical data), but CROs and CRAs would only be able to access information about the sites and possibly aggregated information about the patients, so as to protect patients' anonymity. (Clinical system 30 may provide appropriate authentication and/or authorization services to that end).

FIG. 7 is a chart illustrating key time points at which users may have or may be provided with incentives to provide, update or confirm information, such as with reference to step 225 in FIG. 2 or step 325 in FIG. 3. Users 702 may include PIs, sites or their personnel such as nurses and administrators as well as third-party vendors to sites, patients, and sponsors or CROs, including their personnel, such as CRAs or site monitors. Key time points 704 include study design, site selection, subject enrollment, study execution, and site payment milestones. The time points are roughly ordered, may overlap, and may include discrete sub time points, as in study execution, which may include randomization, multiple patient visits, and study completion. Incentives at some key time points may include 710 a PI providing feedback on study design in order to be considered for that trial; a sponsor or CRO 740 sharing a study design to receive timely feedback in order to avoid later protocol amendments or to consider more efficient study designers; a PI 715 and/or site 720 desiring to keep certifications up to date or other information relevant to site selection in order to be volunteer for or be considered as candidates for trials; sites 730 desiring to maintain shipping and personnel information in order to receive trial supplies; sites 735 desiring to maintain any site-related data in order to timely receive site payments for their participation in a study; sponsors or CROs 750 desiring to utilize the present invention in order to provide more efficient, streamlined payments to sites; and patients 725 desiring to be considered as candidates for studies, to have access to documents such as signed informed consent documents (ICDs), or may be incentivized with gamefication techniques to provide, maintain or confirm information.

With respect to advantages of the present invention as illustrated with reference to FIG. 6, the incentives at key time points also facilitate indirect linkage between patients and sponsors or CROs, who may otherwise have no direct contact or communication to patients due to the nature of clinical trials and privacy regulations. Additionally, with respect to the collaboration required for clinical protocol review in order to avoid later unnecessary amendments, a sponsor or CRO 840 may desire to take advantage of a site and/or PI-based community while maintaining the confidentiality of the proposed study from other sponsors.

Figure 8:
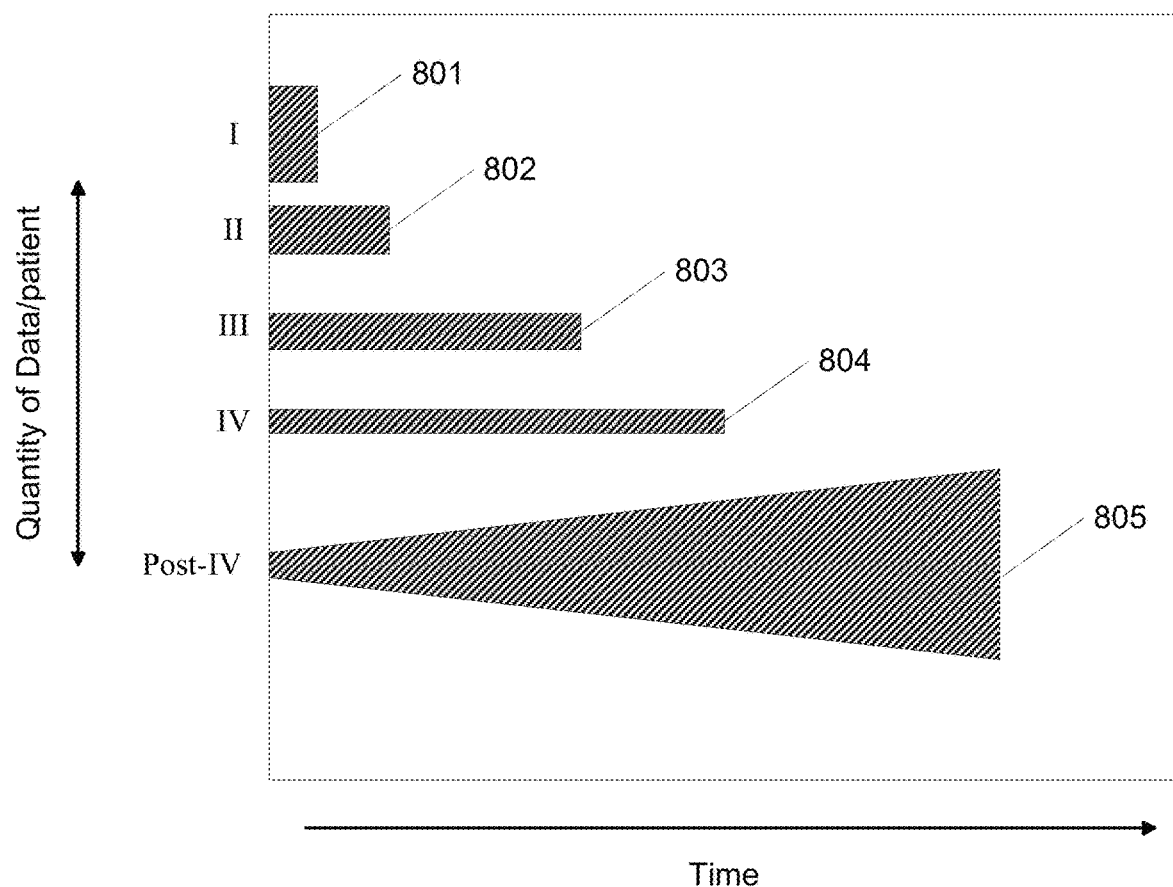
FIG. 8 is a graph illustrating a use of an embodiment of the present invention.

FIG. 8 is a graph illustrating a use of an embodiment of the present invention. The graph shows typical scope or quantity of data per patient that may be collected during clinical trials in phases I, II, III, and IV. In a Phase I trial, relatively few patients may provide data for a relatively short time, as shown with area 801. A Phase II trial may last longer than a Phase I trial, and may collect less data for each patient, as shown with area 802. A Phase III trial may be even more focused than a Phase II trial, may last longer, and may include more patients, so the amount of data per patient may decrease, as shown with area 803. Finally, during Phase IV (after the drug begins to be marketed), there may be more subjects and monitoring may take longer, but the amount of data per patient may continue to decrease, as shown with area 804.

In reality, however, there may be a wealth of data that may be generated after Phase IV, which quantity of data may increase per patient or subject as time progresses, as shown in area 805. Duration here may be ten years or more, and the data generated may include information about patients other than a narrow use of the specific drug under investigation. Using master database 100, it may be possible to keep track of patient information over the extended time period shown in area 805, and then correlate these changes and other information to use of the drug. Currently, there is no mechanism for CROs or sponsors to track use of a drug and other information over such an extended time, and there may be privacy, confidentiality, and anonymity concerns were the sponsor or CRO attempt to do so, including subject blinding requirements. But the database operator may not be under such constraints, and may be able to maintain the database and add long-term information to the master record for such patients.

The previous embodiments are described in the setting up of a master database for use with clinical trials. It is understood, however, that embodiments of the invention can be used in other fields involving database maintenance, such as online merchandising.

Some of the benefits of the present invention are that clinical sites may be selected and clinical trials may be started more quickly because of easier investigator and site selection, site selection costs may be reduced, site performance may be increased because the administrative burden on site personnel is reduced, and drug-to-market probability may be increased through better site selection and/or performance. In some cases, costs may be reduced and better sites selected by avoiding sites having poor feedback and performance scores. Other benefits include the ability to receive feedback from other PIs or site personnel during the study design process, including feedback on study design/protocols. Such feedback may be facilitated by the generation of master records, whereby the PIs, site personnel, studies, sites, etc., and their relationships have been determined.

In some instances, having more information about a site helps the site selector make a more-informed decision. For example, some may consider a low-enrolling site to be poor performing, but an understanding of why such a site is low-enrolling is beneficial, and a low-enrolling site may actually be desired, especially since it may become increasingly more difficult to find suitable sites and patients for clinical trials.

Master database generator 10 as well as master database 100 itself may be implemented on a network, for example, over the Internet as a cloud-based service or hosted service, which may be accessed through a standard web service API.

The generated database of the present invention differs from other databases that include users' information. Such databases may not have, e.g., information related to users culled from public and private databases, information about users from other users, or information relevant to clinical trials, based on which metrics related to operational, financial and scientific data may be associated with users. The present invention also differs from other databases that include information related to clinical trials. For example, client companies may have databases that are trial-specific or company-specific, but their breadth is limited to trials sponsored by that specific company. In contrast, master database generator 10 would take input from such trial-specific and company-specific databases, public and private databases, and information from users to generate and maintain a more comprehensive database. Moreover, master database 100 may include information that is beneficial to the users, such as training and certification information, allowing master database 100 to be kept up-to-date, and that information can be used to screen sites and personnel for additional clinical trials.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof, A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method for generating a clinical record in a clinical trial database for a clinical site, comprising:
   executing a matching algorithm to identify clinical data corresponding to the clinical site, said clinical data being received from at least a private and a public database;
   receiving additional information concerning the clinical site;
   identifying a user associated with the clinical site who may confirm the clinical data from the first database and the second database;
   requesting the user to confirm the clinical data;
   receiving a plurality of confirmations, corrections, or both from the user;
   adding to the clinical record clinical trial information about the clinical site; and
   training the matching algorithm based on the confirmations and corrections,
   wherein the matching algorithm improves as more confirmations and corrections are received, and improvement of the algorithm allows the algorithm to generalize to unseen situations by using a degree of confidence to identify clinical data corresponding to the clinical site.

2. The method of claim 1, wherein the clinical trial information includes data related to performing clinical trials.

3. The method of claim 2, wherein said public database and said private database are disparate.

4. The method of claim 1, wherein the additional information includes data related to the clinical site's credentials.

5. The method of claim 1, wherein the additional information includes data related to the clinical site's training.

6. The method of claim 1, wherein the additional information includes data related to the clinical site's a certification.

7. A method for generating a master clinical record in a master clinical database, comprising:
   receiving at the master clinical database, utilizing a processor, data from at least a first database that comprises at least a record;
   executing a matching algorithm to identify the received data corresponding to data received from a second database that comprises at least a record;
   calculating a match for the corresponding data, wherein said calculation determines a degree of confidence based on training data received from a user, wherein said training data comprises confirmations and corrections to the matching algorithm,
   wherein the matching algorithm improves as more confirmations and corrections are received, and improvement of the algorithm allows the algorithm to generalize to unseen situations by using a degree of confidence to identify clinical data corresponding to the clinical site;
   determining whether the degree of confidence is greater than or equal to a threshold confidence level;
   determining that the degree of confidence is less than the threshold confidence level, and identifying a user who may confirm the corresponding data;
   requesting, at a time point, from the user confirmation of the corresponding data;
   receiving said confirmation from the user at the time point;
   updating the received data from the first and second databases with said confirmation;
   repeating said steps of calculating, determining, and requesting, receiving, and correlating said confirmation until the degree of confidence is greater than or equal to the threshold confidence level; and
   if said degree of confidence is greater than or equal to the threshold confidence level, updating the master clinical database by confirming said updated data comprises a master clinical record.

8. The method of claim 7, wherein:
said requesting confirmation further comprises retrieving a workflow, said workflow comprising users, tasks, and time points, wherein said tasks are executable at said time points; and
said identifying a user is based on the retrieved workflow.

9. The method of claim 7, wherein said threshold confidence level is adjustable by a user.

10. The method of claim 8, wherein said time points are further associated with one or more incentives, and wherein said requesting confirmation is accompanied by said incentives.

11. The method of claim 10, wherein said identifying is further based on users having associated incentives.

12. The method of claim 8, wherein said first database is a public database and wherein said second database is a private database.

13. The method of claim 12, wherein said master clinical record is accessed while maintaining confidentiality requirements.

14. The method of claim 12, wherein said master clinical record is augmented by user curation.

15. A non-transitory computer readable storage medium, comprising computer executable instructions embodied therein, to be executed by a computer, for:
executing a matching algorithm to identify clinical data corresponding to a clinical site, said clinical data being received from at least one public database and at least one private database;
identifying, based on a retrieved workflow, at least one user associated with the clinical site, wherein the workflow consists of users, tasks, and time points, wherein the tasks are executable at said time points;
receiving additional information from said at least one user concerning the clinical site, said information comprising a plurality of confirmations, corrections, or both;
requesting, at one or more of the time points, said at least one user to confirm the corresponding clinical data; and
adding to a clinical record clinical trial information about the performance of the clinical site; and
training the matching algorithm based on the confirmations and corrections,
wherein the matching algorithm improves as more confirmations and corrections are received, and improvement of the algorithm allows the algorithm to generalize to unseen situations by using a degree of confidence to identify clinical data corresponding to the clinical site.

16. The non-transitory computer readable storage medium of claim 15, further comprising computer executable instructions whereby said time points are further associated with one or more incentives, and wherein said identifying is accompanied by said incentives.

17. The method of claim 7, wherein said threshold confidence level is predetermined by a user.

* * * * *

UNITED STATES PATENT AND TRADEMARK OFFICE
CERTIFICATE OF CORRECTION

PATENT NO. : 10,515,060 B2
APPLICATION NO. : 14/066421
DATED : December 24, 2019
INVENTOR(S) : de Vries et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*